United States Patent
Furukawa et al.

(10) Patent No.: US 11,529,093 B2
(45) Date of Patent: Dec. 20, 2022

(54) INTRAORAL MOISTURE MEASURING DEVICE

(71) Applicant: KABUSHIKIKAISHA RAIFU, Koshigaya (JP)

(72) Inventors: Makoto Furukawa, Saitama (JP); Ryuki Sato, Saitama (JP); Jun Furukawa, Saitama (JP)

(73) Assignee: KABUSHIKIKAISHA RAIFU, Koshigaya (JP)

( * ) Notice: Subject to any disclaimer, the term of this patent is extended or adjusted under 35 U.S.C. 154(b) by 864 days.

(21) Appl. No.: 16/250,261

(22) Filed: Jan. 17, 2019

(65) Prior Publication Data
US 2019/0183407 A1 Jun. 20, 2019

Related U.S. Application Data

(62) Division of application No. 14/896,675, filed as application No. PCT/JP2014/053846 on Feb. 19, 2014, now Pat. No. 10,219,735.

(51) Int. Cl.
*A61B 5/0537* (2021.01)
*A61B 5/00* (2006.01)

(52) U.S. Cl.
CPC .......... *A61B 5/4277* (2013.01); *A61B 5/0537* (2013.01); *A61B 5/4552* (2013.01); *A61B 5/6843* (2013.01); *A61B 5/7405* (2013.01); *A61B 2560/029* (2013.01); *A61B 2560/0266* (2013.01); *A61B 2560/0425* (2013.01);
(Continued)

(58) Field of Classification Search
CPC ... A61B 5/4277; A61B 5/0537; A61B 5/4552; A61B 5/6843; A61B 5/7405; A61B 2560/0266; A61B 2560/029; A61B 2560/0425; A61B 2560/0443; A61B 2560/0468; A61B 2562/0214; A61B 2562/0247; A61B 2562/0261; A61B 2562/029

See application file for complete search history.

(56) References Cited

U.S. PATENT DOCUMENTS

| 5,660,168 A | 8/1997 | Ottosson et al. |
| 2013/0274566 A1 | 10/2013 | Koyama et al. |

(Continued)

FOREIGN PATENT DOCUMENTS

| EP | 1 543 768 A1 | 6/2005 |
| JP | 61-140830 A | 6/1986 |

(Continued)

OTHER PUBLICATIONS

English (Machine) Translation of JP 61-140830A (Year: 1986).*

*Primary Examiner* — Daniel L Cerioni
(74) *Attorney, Agent, or Firm* — Flynn Thiel, P.C.

(57) ABSTRACT

An intraoral moisture measuring device includes: a swing member that swings with respect to a main body about a predetermined swing center; a moisture amount detection unit provided at a tip of the swing member, for detecting a moisture amount by being directly or indirectly abutted against a measurement site in a mouth; and a biasing member for biasing the swing member in one of swing directions. Consequently, the intraoral moisture measuring device is capable of measuring intraoral moisture in a simple and highly-accurate manner.

2 Claims, 9 Drawing Sheets

(52) U.S. Cl.
CPC ........ *A61B 2560/0443* (2013.01); *A61B 2560/0468* (2013.01); *A61B 2562/029* (2013.01); *A61B 2562/0214* (2013.01); *A61B 2562/0247* (2013.01); *A61B 2562/0261* (2013.01)

(56) References Cited

U.S. PATENT DOCUMENTS

| | | | |
|---|---|---|---|
| 2014/0018641 A1 | 1/2014 | Yoshino et al. | |
| 2015/0031964 A1* | 1/2015 | Bly | A61B 5/681 600/301 |
| 2015/0371522 A1 | 12/2015 | Mravyan et al. | |

FOREIGN PATENT DOCUMENTS

| | | |
|---|---|---|
| JP | 7-327937 A | 12/1995 |
| JP | 8-502179 A | 3/1996 |
| JP | 2003-169788 A | 6/2003 |
| JP | 2005-205041 A | 8/2005 |
| JP | 2006-122347 A | 5/2006 |
| JP | 4417841 B2 | 2/2010 |
| JP | 2013-66565 A | 4/2013 |
| JP | 2013-132516 A | 7/2013 |
| JP | 2013-195118 A | 9/2013 |

\* cited by examiner

INTRAORAL MOISTURE MEASURING DEVICE

CROSS REFERENCE TO RELATED APPLICATION

This is a divisional of U.S. Ser. No. 14/896,675, filed Dec. 8, 2015, which is the national stage application of PCT/JP2014/053846, filed Feb. 19, 2014.

TECHNICAL FIELD

The present invention relates to an intraoral moisture measuring device for measuring intraoral moisture.

BACKGROUND ART

Conventionally, xerostomia, called dry mouth, is generally considered to be developed, for example, by systematic illness such as diabetes or renal disease, mouth breathing or smoking, side effects of medicine or treatment, salivary gland disease, central or peripheral nervous disorder, or psychological stress. Xerostomia is often found especially in the elderly. It has been reported that approximately 40% of the elderly suffer from xerostomia.

In Japan, starting with the research of "About xerostomia in the elderly and the physical properties of saliva" in Comprehensive Research Project on Longevity Science by Ministry of Health, Labor and Welfare in 2001 to 2003, various researches have been made, for example, on actual conditions of xerostomia in the elderly and the effectiveness of oral care for the prevention of aspiration pneumonitis. As a result of this, active oral care systems have been introduced, for example, in the National Cancer Center which practices advanced cancer therapy and palliative care. In the revisions on medical treatment fees in fiscal year 2012, the "perioperative oral management fee for cancer patients" has been introduced into insurance based on these systems.

It is important for oral care to measure intraoral moisture accurately. In recent years, an intraoral moisture measuring device including a capacitance type sensor is increasingly used (see Patent Literature 1, for example). For such a capacitance type intraoral moisture measuring device, a moisture amount in mucosa is measured on the basis of a change in capacitance between two electrodes. Therefore, the sensor unit needs to be abutted against a measurement site with a suitable pressing force (load). Thus, when a user is inexperienced in using the intraoral moisture measuring device, there is a risk of producing variations in the measurement result.

As a countermeasure against such a problem, a technique has been proposed in which a sensor is disposed in a slider, which is biased in a pressing direction by a spring, in a skin moisture measuring device, for example, and the magnitude of a pressing force is determined on the basis of a travel distance of the slider (see Patent Literature 2). Also, another technique has been proposed in which a sensor holding structure, capable of easily deforming, is disposed on the rear side of a sensor in an intraoral moisture measuring device, so that the direction of the sensor can be freely changed when being pressed (see Patent Literature 3).

CITATION LIST

Patent Literature

Patent Literature 1: Japanese Patent No. 4417841
Patent Literature 2: Japanese Patent Application Laid-Open No. 2003-169788
Patent Literature 3: Japanese Patent Application Laid-Open No. 2005-205041

SUMMARY OF INVENTION

Technical Problem

With the technique described in Patent Literature 2, however, the structure in the vicinity of the sensor becomes complicated, and it is therefore difficult to apply such a technique to an intraoral moisture measuring device which requires the sensor to be inserted into a narrow space in a mouth. Furthermore, since too much cost is needed for replacement, it is difficult to make the sensor and its adjacent parts disposable (expendable). With the technique described in Patent Literature 3, the direction of the sensor is freely changed by the sensor holding structure. Thus, a pressure sensor needs to be disposed on the rear side of the sensor in order to measure a pressing force. This leads to a complicated and high-cost structure in the vicinity of the sensor. Again, it is difficult to make such a structure disposable.

The new diagnostic criteria for the Sjogren syndrome, which produces xerostomia as its prominent symptom, includes labial minor salivary gland biopsy. However, rejection against biopsy is often seen in medical practice, and therefore the emergence of an intraoral moisture measuring device capable of measuring even the state of a labial minor salivary gland, which is present at a relatively deep position under the labial mucosa, with high accuracy has been desired as a replacement for the biopsy.

In view of such circumstances, it is an object of the present invention to provide an intraoral moisture measuring device capable of measuring intraoral moisture in a simple and highly-accurate manner.

Solution to Problem

The present invention is an intraoral moisture measuring device including: a swing member that swings with respect to a main body about a predetermined swing center; a moisture amount detection unit provided at a tip of the swing member, for detecting a moisture amount by being directly or indirectly abutted against a measurement site in a mouth; and a biasing member for biasing the swing member in one of swing directions.

The present invention is characterized in that the swing center is disposed in the main body in the intraoral moisture measuring device with the above-mentioned means.

The present invention is characterized in that the intraoral moisture measuring device with the above-mentioned means includes a pressing force detection unit for detecting a pressing force to the measurement site by the moisture amount detection unit.

The present invention is characterized in that the pressing force detection unit is disposed inside the main body in the intraoral moisture measuring device with the above-mentioned means.

The present invention is characterized in that the intraoral moisture measuring device with the above-mentioned means includes a control unit for controlling the moisture amount detection unit and the pressing force detection unit, and the control unit includes pressing force determination means for determining if the pressing force detected by the pressing force detection unit falls within an appropriate range.

The present invention is characterized in that the control unit includes measurement starting means that starts moisture amount measurement when the pressing force detected by the pressing force detection unit falls within the appropriate range in the intraoral moisture measuring device with the above-mentioned means.

The present invention is characterized in that the control unit includes measurement stopping means for stopping moisture amount measurement when the pressing force detected by the pressing force detection unit falls outside the appropriate range in the intraoral moisture measuring device with the above-mentioned means.

The present invention is characterized in that the swing member is configured to be at least partially detachable from the main body together with the moisture amount detection unit in the intraoral moisture measuring device with the above-mentioned means.

The present invention is characterized in that, in the intraoral moisture measuring device with the above-mentioned means, the swing member includes a detachable part that is detachable from the main body together with the moisture amount detection unit, the detachable part is provided with a first electrode and a second electrode included in the moisture amount detection unit and wirings connected to the first electrode and the second electrode, and the first electrode, the second electrode, and the wirings are formed by electrically-conductive thin films disposed in the detachable part.

The present invention is characterized in that the wirings are covered with a shield formed by an electrically-conductive thin film in the intraoral moisture measuring device with the above-mentioned means.

The present invention is characterized in that the intraoral moisture measuring device with the above-mentioned means includes a support member for supporting a rear side of the measurement site.

The present invention is characterized in that the support member includes a protrusion protruded toward the rear side of the measurement site, and the protrusion includes a generally flat-shaped surface to be abutted against the rear side of the measurement site in the intraoral moisture measuring device with the above-mentioned means.

Advantageous Effects of Invention

The intraoral moisture measuring device according to the present invention can provide an excellent effect in that intraoral moisture can be measured in a simple and highly-accurate manner.

DESCRIPTION OF EMBODIMENTS

Embodiments of the present invention will be described below with reference to the accompanying drawings.

Figure 1:
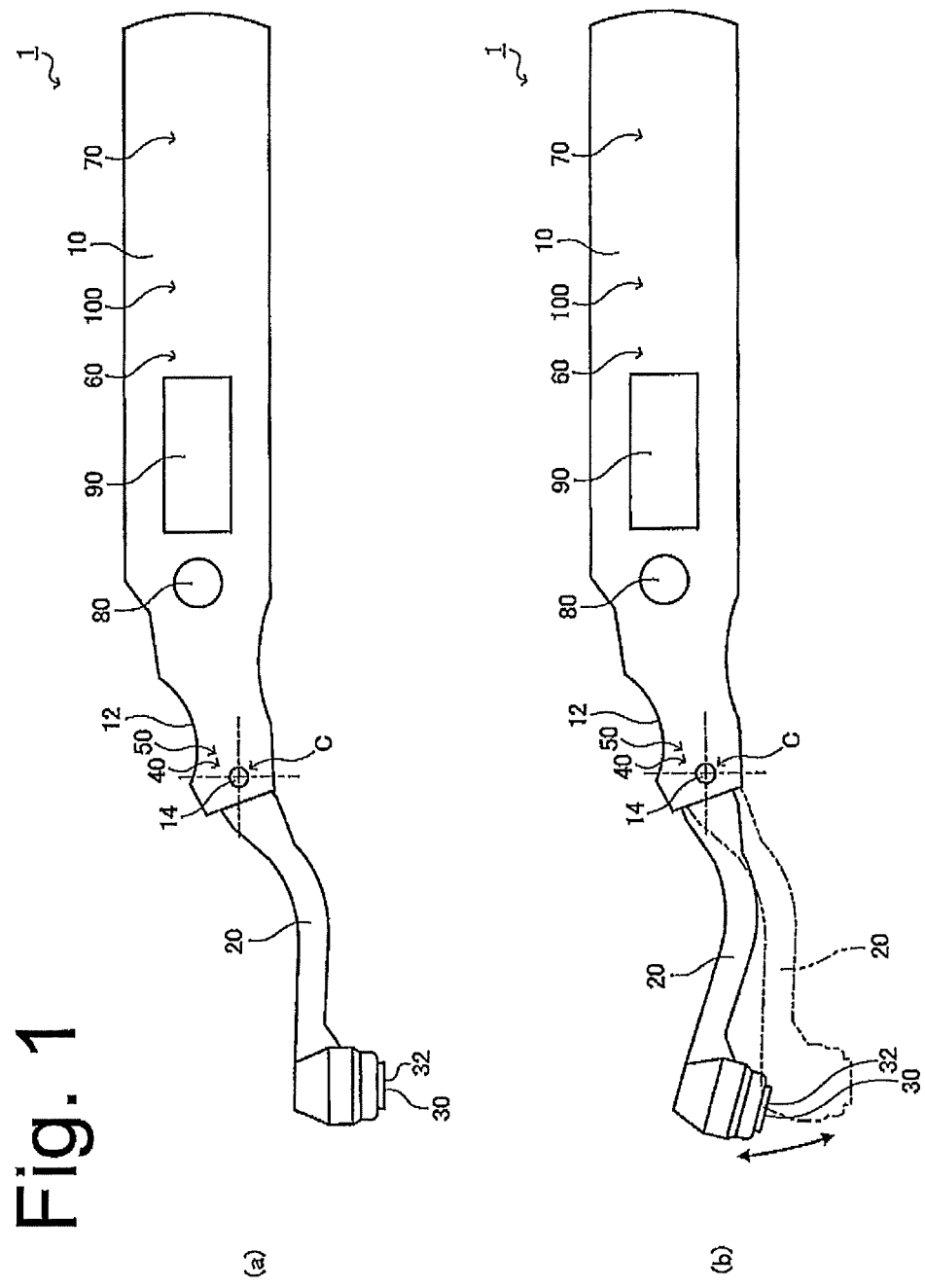
FIG. 1 and parts (a) and (b) thereof are schematic front views illustrating an intraoral moisture measuring device according to a first embodiment of the present invention.
Figure 2:
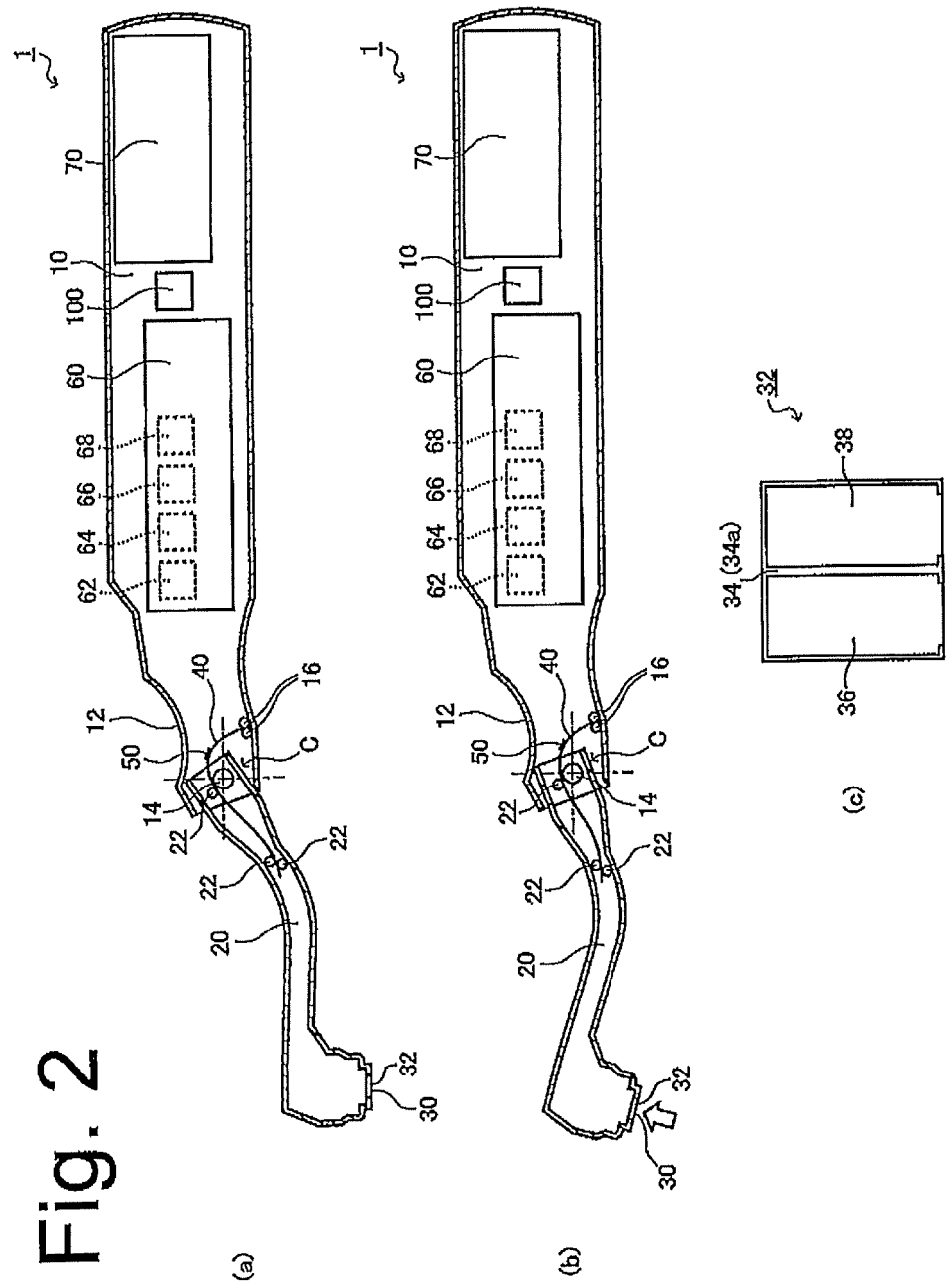
FIG. 2 and parts (a) and (b) thereof are schematic cross-sectional views of the intraoral moisture measuring device.

First, an intraoral moisture measuring device 1 according to a first embodiment of the present invention will be described. FIGS. 1(a) and 1(b) are schematic front views illustrating the intraoral moisture measuring device 1 according to this embodiment. FIGS. 2(a) and 2(b) are schematic cross-sectional views of the intraoral moisture measuring device 1. As shown in these figures, the intraoral moisture measuring device 1 (hereinafter simply referred to as the measuring device 1) includes: a main body 10 having a generally bar shape; a swing member 20 swingably supported by the main body 10; a moisture amount detection unit 30 provided on the tip side of the swing member 20; a biasing member 40 for biasing the swing member 20; a pressing force detection unit 50 disposed in the biasing member 40; a control unit 60 and a power supply unit 70 provided inside the main body 10; an operation button 80 and a display unit 90 disposed on the front side of the main body 10; and a sound output unit 100 disposed inside the main body 10.

The main body 10 is a part for supporting or housing respective components of the measuring device 1 as well as a part to be grasped by a user. The main body 10 is formed in a generally bar shape and provided with a dent 12, disposed in an upper portion closer to the swing member 20, on which an index finger tip of a user is placed. In other words, the main body 10 is configured so that a user can grasp the main body 10 in the same manner as that of holding a pencil. Moreover, the operation button 80 is disposed at a position where a user can operate the operation button 80 with a thumb while holding the main body 10. The display unit 90 is disposed at a position where the user can visually check the display unit 90 while holding the main body 10. Although the operation button 80 and the display unit 90 are disposed on the basis of the premise of use by a right hand in this embodiment, the main body 10 may be configured for a left-hander by disposing the operation button 80 and the display unit 90 on the rear side. Needless to say, the manner of holding the main body 10 is not limited to that of holding a pencil. For example, another manner of holding the main body 10 such as placing the tip of a thumb on the dent 12 may be selected.

The swing member 20 supports the moisture amount detection unit 30 and swings together with the moisture amount detection unit 30. The swing member 20 is supported via a swing shaft 14 provided on the left side of the main body 10 as viewed from the front with the axial direction thereof coinciding with the front-back direction. As shown in FIG. 1(b), the swing member 20 is swingable with respect to the main body 10 with a center C of the swing shaft 14 serving as the swing center. In other words, the swing member 20 is configured to swing by a pressing force generated when the moisture amount detection unit 30 provided on the tip side thereof is pressed against a measurement site. Moreover, the swing member 20 is formed in such a shape that a stick-like member is bent in a generally dogleg shape. Consequently, the moisture amount detection unit 30 is disposed at a position and with an orientation such that the moisture amount detection unit 30 can be easily abutted against the measurement site when a user holds the main body 10.

A swing range (swing angle range) of the swing member 20 is not limited to any particular range. In order to facilitate the adjustment of the pressing force, however, the swing range of the swing member 20 is preferably 10° or more and 20° or less, and more preferably 13° or more and 15° or less. Needless to say, the shape of the swing member 20 is not limited to the shape bent in the generally dogleg shape, and other shapes may be employed instead.

The moisture amount detection unit 30 is a part to be directly or indirectly abutted against lingual mucosa, buccal mucosa, palatine mucosa, labial mucosa, or the like in the mouth of a subject to be measured in order to detect a moisture amount in that site (i.e., the measurement site). The moisture amount detection unit 30 includes a capacitance type sensor 32 controlled by the control unit 60. FIG. 2(c) is a schematic view illustrating a structure of the sensor 32. The sensor 32 includes: a substrate 34 which is an insulator having a generally square plate shape; and a first electrode 36 and a second electrode 38 which are electrically-conductive thin films formed on a surface 34a of the substrate 34. In other words, the sensor 32 measures an amount of moisture, which is an electrical conductor present around the sensor 32, on the basis of a capacitance change between the first electrode 36 and the second electrode 38.

In this embodiment, the first electrode 36 and the second electrode 38 are each formed in a generally rectangular shape as shown in FIG. 2(c). This makes it possible to downsize the sensor 32 without deteriorating the detection sensitivity of moisture. Note however that the shape of the first electrode 36 and the second electrode 38 is not limited to the rectangular shape. Another shape such as a comb teeth shape, for example, may be employed instead.

A suitable material such as a resin or ceramic, for example, may be employed as a material for the substrate 34. A suitable material such as copper or aluminum, for example, may be employed as a material for the first electrode 36 and the second electrode 38. In order to improve the corrosion resistance of the sensor 32, gold plating, for example, may be applied on the surfaces of the first electrode 36 and the second electrode 38, or the first electrode 36 and the second electrode 38 may be covered with an insulating resin coating, for example.

The biasing member 40 is configured to bias the swing member 20 in one of swing directions. In this embodiment, the biasing member 40 is a flat spring made of a suitable metal and disposed so as to run over the inside of the main body 10 and the inside of the swing member 20. The biasing member 40 is configured to bias the swing member 20 in a direction in which the moisture amount detection unit 30 is pressed against the measurement site by being held by a holding member 16 provided in the main body 10 and a holding member 22 provided in the swing member 20. In other words, in this embodiment, by causing the moisture amount detection unit 30 to be pressed against the measurement site and thereby causing the swing member 20 to suitably swing, elastic deformation suitably occurs in the biasing member 40 as shown in FIG. 2(b). Due to the restoring force of this elastic deformation, an appropriate pressing force is generated.

The range of the appropriate pressing force against the measurement site by the moisture amount detection unit 30 is not limited to any particular range. Such a range is determined according to the depth of a position where a moisture amount is measured from a mucous surface or the characteristics of the sensor 32, for example. In view of the ease of the measuring operation, the swing angle of the swing member 20 by which the biasing member 40 can generate a pressing force in the appropriate range preferably falls in a range of 30% or more and 70% or less in the swing range of the swing member 20. Moreover, the main body 10 or the swing member 20 may be calibrated, for example, so that whether a swing angle for generating an appropriate pressing force is achieved can be visually checked.

The pressing force detection unit 50 is a part that is controlled by the control unit 60 and detects a pressing force against the measurement site by the moisture amount detection unit 30. In this embodiment, the pressing force detection unit 50 is constituted by a strain gauge disposed in the biasing member 40 inside the main body 10 and having a known structure. In other words, the pressing force detection unit 50 is configured to detect a pressing force on the basis of a strain amount in the elastic deformation of the biasing member 40.

In this embodiment, the swing member 20 is swung when the moisture amount detection unit 30 is pressed against the measurement site. This makes it possible to apply the pressing force in the moisture amount detection unit 30 to the biasing member 40 after the amplification thereof by a lever ratio. This can increase the actual force detected by the pressing force detection unit 50 and thereby enhance the resolution. Thus, the detection of the pressing force can be performed with higher accuracy. Moreover, providing the swing member 20 allows the biasing member 40 that generates a pressing force and the pressing force detection unit 50 that detects the pressing force to be disposed on the main body 10 side so as to be away from the moisture amount detection unit 30. This makes it possible to configure a simple and compact portion in the vicinity of the moisture amount detection unit 30.

The control unit 60 controls the moisture amount detection unit 30, the pressing force detection unit 50, and other components of the measuring device 1. The control unit 60 includes a suitable microcomputer chip including a CPU, a ROM, a RAM, and the like, as well as various circuits such as an oscillation circuit for the sensor 32. The control unit 60 is electrically connected to the respective components of the measuring device 1 through wiring (not shown) or the like.

As functional configurations achieved by the execution of programs by the CPU, the control unit 60 also includes: moisture amount measuring means 62 for measuring a moisture amount by controlling the moisture amount detection unit 30; pressing force measuring means 64 for measuring a pressing force by controlling the pressing force detection unit 50; pressing force determination means 66 for determining if the pressing force detected by the pressing force detection unit 50 falls within the appropriate range; and measurement starting means 68 for starting moisture amount measurement when the pressing force detected by the pressing force detection unit 50 falls within the appropriate range. The details of the respective functional configurations of the control unit 60 will be described later.

The power supply unit 70 is configured to house a dry cell or a rechargeable battery, for example, and supplies power to the control unit 60 and other components. The operation button 80 is provided for various operations such as an ON/OFF operation of the power supply and mode switching operation. The display unit 90 is constituted by a liquid crystal panel, for example, and displays a variety of information such as measurement results. The sound output unit 100 is constituted by a suitable speaker and outputs sound such as various types of notification sound.

Figure 3:
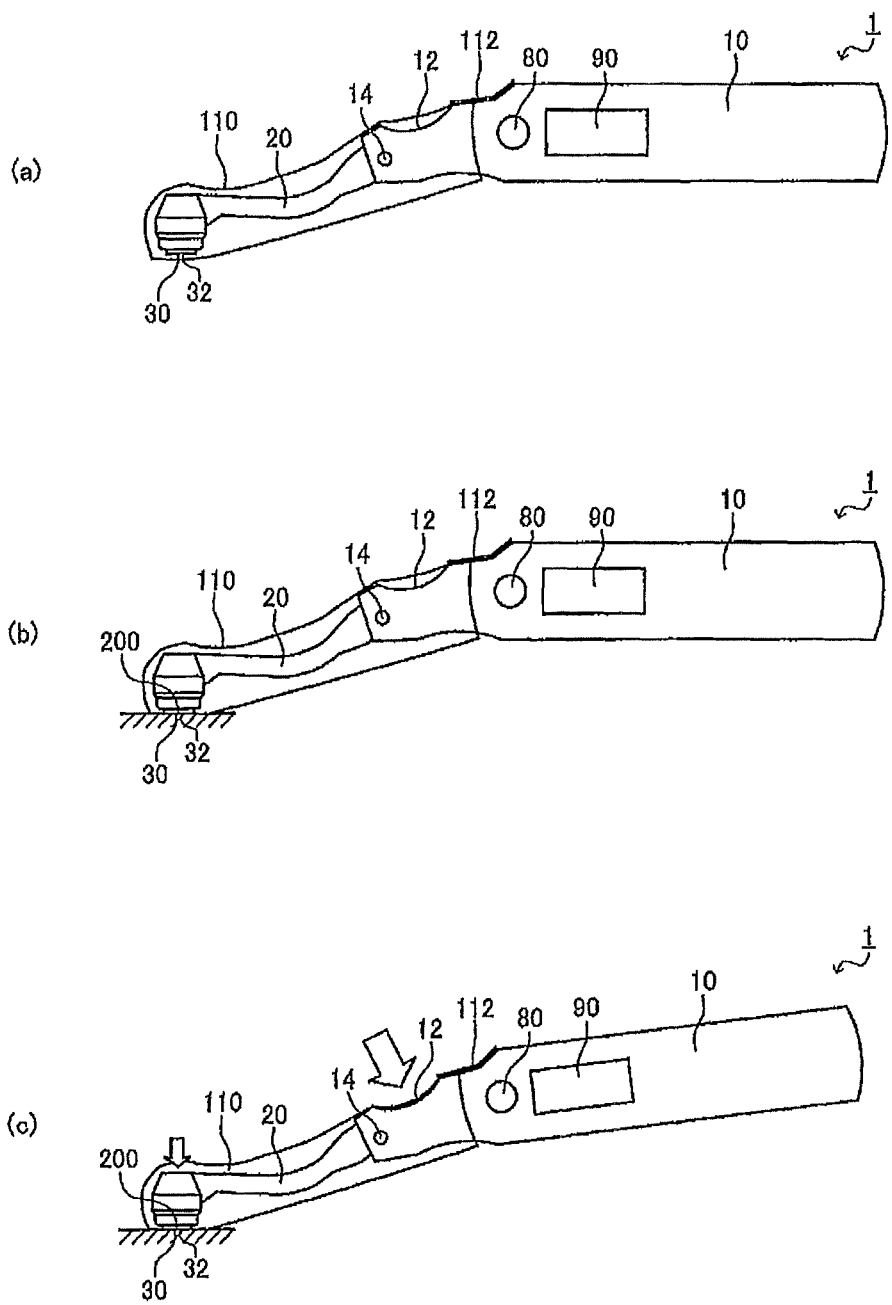
FIG. 3 and parts (a) to (c) thereof are schematic views illustrating a method of using the intraoral moisture measuring device.

A method of using the measuring device 1 will be described next. FIGS. 3(a) to 3(c) are schematic views illustrating the method of using the measuring device 1. In order to measure intraoral moisture by the measuring device 1, firstly, a bag-shaped cover 110 is attached so as to cover the moisture amount detection unit 30, the swing member 20, and part of the main body 10 as shown in FIG. 3(a).

The cover 110 is formed by a suitable insulating resin film. The attachment of the cover 110 prevents short circuit between the first electrode 36 and the second electrode 38 from occurring when the moisture amount detection unit 30 is pressed against the measurement site in a mouth. Moreover, the cover 110 can prevent the moisture amount detecting unit 30 and the swing member 20 from being directly brought into contact with the mucosa or skin of a subject to be measured. Also, by replacing the cover 110 for each measurement or for each subject to be measured, the measuring device 1 can be kept in an appropriate hygienic condition, and thus various infections or the like can be prevented. In order to prevent, for example, dropping off or accidental ingestion of the cover 110 during measurement, it is preferable that the cover 110 be fixed to the main body 10 with a suitable adhesive sheet 112 or the like.

Once the cover 110 is appropriately attached, the operation button 80 is operated to turn on the power supply of the measuring device 1. This starts the measurement of a pressing force by the pressing force measuring means 64. Next, as shown in FIG. 3(b), positioning is performed by causing the moisture amount detection unit 30 to be brought into lightly contact with a measurement site 200 in the mouth of a subject to be measured. Once the position of the moisture amount detection unit 30 is set, the swing member 20 is suitably swung by pushing the dent 12 with an index finger or a thumb, for example, as shown in FIG. 3(c). This causes the moisture amount detection unit 30 to be pressed against the measurement site 200 with an appropriate pressing force due to the biasing force of the biasing member 40. The measurement of a moisture amount is thereby started by the moisture amount measuring means 62.

Figure 4:
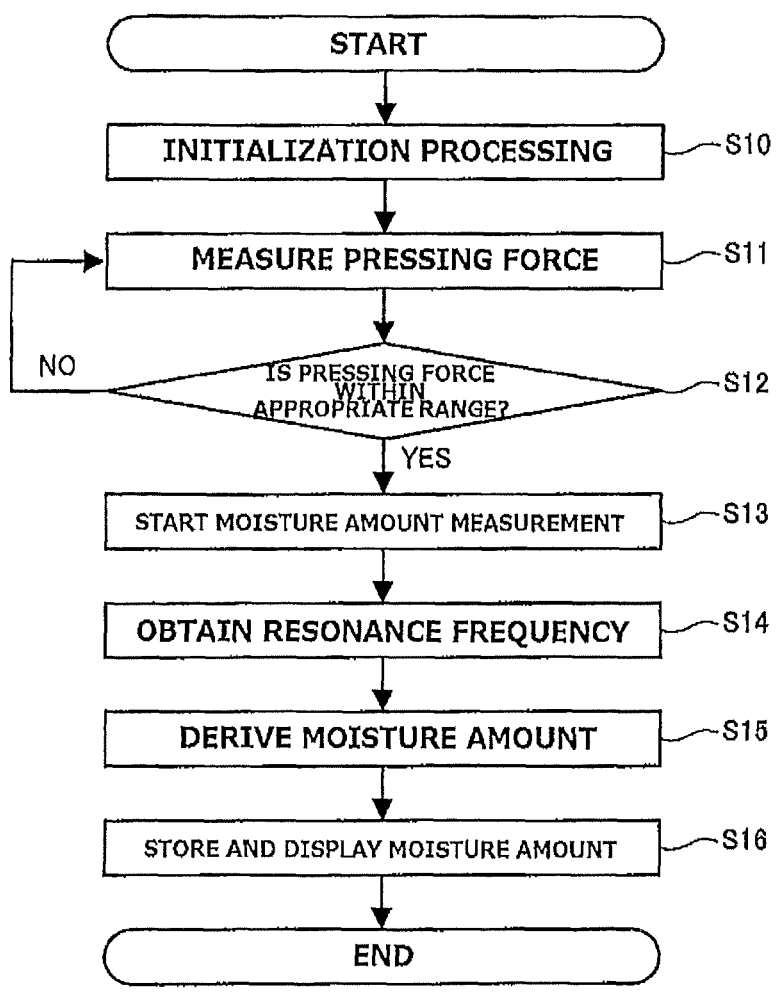
FIG. 4 is a flow chart illustrating a general outline of an operational procedure of a control unit.

Next, an operational procedure of the control unit 60 and the respective functional configurations of the control unit 60 will be described in detail. FIG. 4 is a flow chart illustrating a general outline of the operational procedure of the control unit 60. First, the control unit 60 executes a variety of initialization processing after the power supply is turned on in step S10. The control unit 60 starts the measurement of a pressing force in step S11. Here, the pressing force measuring means 64 measures the pressing force on the basis of an output from a bridge circuit connected to the pressing force detection unit 50 and stores the pressing force in the RAM or the like.

The control unit 60 determines if the measured pressing force falls within a preset appropriate range in step S12. Here, the pressing force determination means 66 determines if the measured pressing force falls within the appropriate range by comparing the value of the measured pressing force with the upper limit value and the lower limit value of the appropriate pressing force range stored in the ROM or the like. When the measured pressing force falls within the appropriate range, the procedure proceeds to step S13. When the measured pressing force falls outside the appropriate range, the procedure returns to step S11 to measure the pressing force again.

In step S13, the control unit 60 starts to measure a moisture amount. Here, the measurement starting means 68 causes the moisture amount measuring means 62 to start the moisture amount measurement on the basis of the determination result of the pressing force determination means 66. Moreover, the measurement starting means 68 controls the sound output unit 100 so as to output notification sound for informing about the start of the moisture amount measurement and also controls the display unit 90 so as to display that the moisture amount is being measured.

The control unit 60 obtains a resonance frequency in the sensor 32 in step S14. Here, the moisture amount measuring means 62 controls the oscillation circuit so as to search for the resonance frequency in the sensor 32 and stores the obtained resonance frequency in the RAM or the like. The control unit 60 derives the moisture amount on the basis of the obtained resonance frequency in step S15. Here, the moisture amount measuring means 62 derives the moisture amount by comparing the obtained resonance frequency with a table stored in the ROM or the like.

The control unit 60 stores the derived moisture amount in the RAM or the like and causes the display unit 90 to display the derived moisture amount in step S16. Here, the moisture amount measuring means 62 stores the derived moisture amount in the RAM or the like. Moreover, the moisture amount measuring means 62 controls the sound output unit 100 so as to output notification sound for informing about the completion of the moisture amount measurement and also controls the display unit 90 so as to display the derived moisture amount. With the above-described procedure, the measurement of intraoral moisture is completed.

As described above, the measuring device 1 of this embodiment allows the moisture amount detecting unit 30 to be easily abutted against the measurement site 200 with an appropriate pressing force without complicating the structure in the vicinity of the moisture amount detecting unit 30. Moreover, since moisture amount measurement is started after the pressing force is determined to fall within the appropriate range, highly accurate measurement can be performed irrespective of the proficiency level of a user.

In parallel to the search for the resonance frequency in step S14, the measurement of the pressing force and the determining if the pressing force falls within the appropriate range may be performed. If the pressing force falls outside the appropriate range during the search, the sound output unit 100 may be controlled so as to output the notification sound for informing that the pressing force falls outside the appropriate range. Also, the search for the resonance frequency may be stopped and the procedure may be returned to step S11. In other words, measurement stopping means for stopping moisture amount measurement when the pressing force detected by the pressing force detection unit 50 falls outside the appropriate range may be provided as a functional configuration of the control unit 60.

Figure 5:
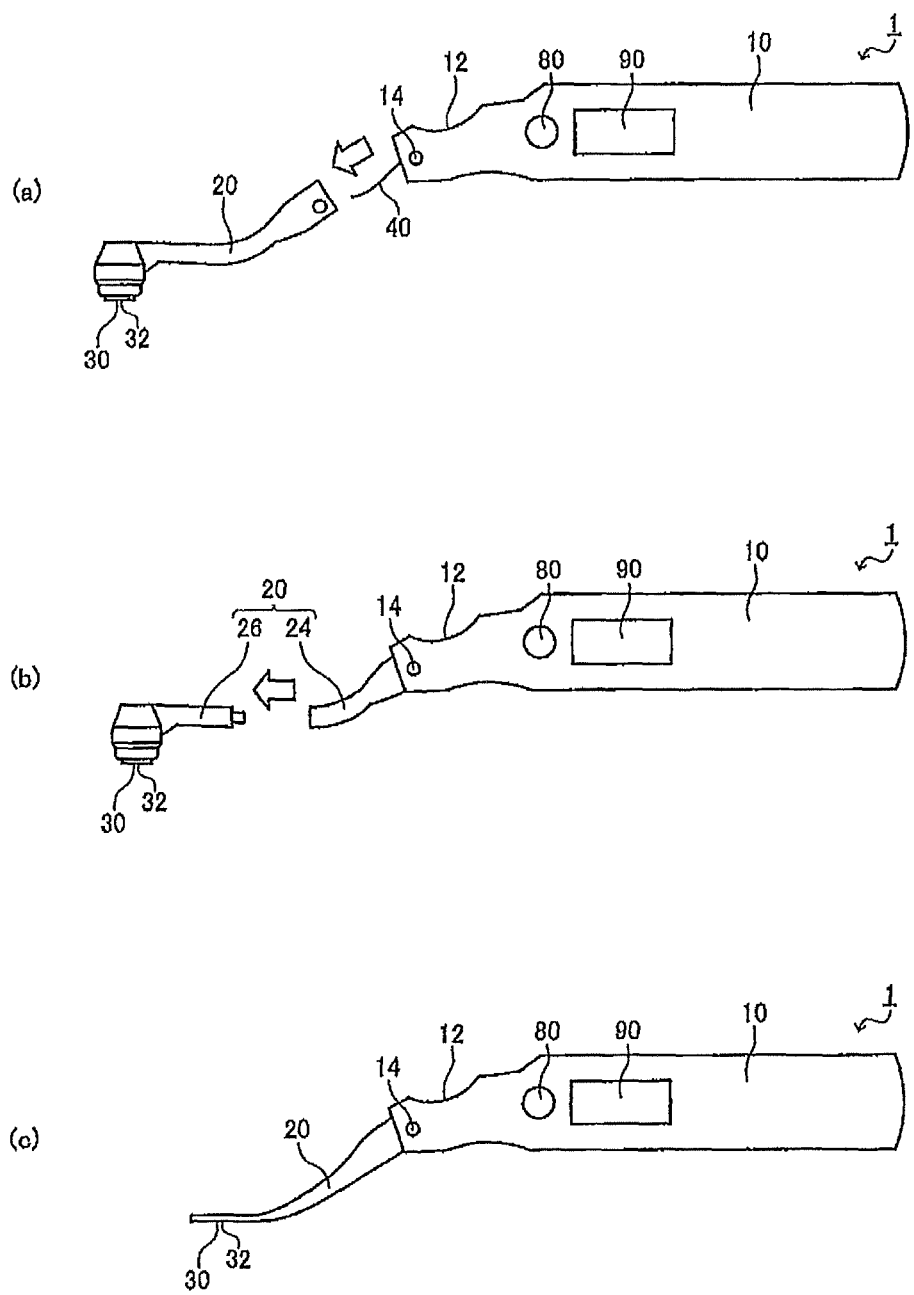
FIG. 5 and parts (a) to (c) thereof are schematic front views illustrating examples in other forms of the intraoral moisture measuring device.

Other forms of the measuring device 1 will next be described. FIGS. 5(a) to 5(c) are schematic front views illustrating examples in other forms of the measuring device 1. FIG. 5(a) illustrates an example of a case where the swing member 20 is configured to be detachable from the main body 10. As just described, the swing member 20 may be configured to be detachable from the main body 10 together with the moisture amount detection unit 30. In this case, the sensor 32 and the control unit 60 may be electrically connected to each other via a suitable connection terminal.

With such a configuration, the moisture amount detection unit 30 and the swing member 20 can be removed from the main body 10, so that they can be easily washed and sterilized, for example. Alternatively, the moisture amount detection unit 30 and the swing member 20 can be made disposable. This makes it possible to keep the hygienic state of the measuring device 1 in a more appropriate state. Especially in this embodiment, the biasing member 40 and the pressing force detection unit 50 are provided on the main body 10 side by providing the swing member 20. This makes it possible to achieve extremely easy washing and sterilization of the portion removed from the main body 10 and to keep the cost low when the moisture amount detection unit 30 and the swing member 20 are made disposable.

Therefore, in this case, the cover 110 may be omitted by covering the surface of the sensor 32 with a suitable insulating resin, for example, and the moisture amount detection unit 30 may directly be abutted against the contact site to measure a moisture amount. In other words, the measuring device 1 of this embodiment can keep an appropriate hygienic condition with low cost not only when the moisture amount detection unit 30 is indirectly abutted against the measurement site via the cover 110 but also when the moisture amount detection unit 30 is directly abutted against the measurement site.

FIG. 5(b) is a schematic front view illustrating an example of a case where the swing member 20 is segmented and a segmented part is configured to be detachable. As just described, the swing member 20 may be comprised of two parts: a fixed part 24 and a detachable part 26. The detachable part 26 may be configured to be detachable from the fixed part 24 and the main body 10 together with the moisture amount detection unit 30. With such a configuration, the removable part can be, in some cases, detached more easily than the case where the entire swing member 20 is made detachable.

FIG. 5(c) is a schematic front view illustrating an example of a case where the moisture amount detection unit 30 is formed in a generally flat plate shape smoothly connected to the swing member 20. As stated above, the biasing member 40 and the pressing force detection unit 50 can be disposed on the main body 10 side in this embodiment. This provides a high flexibility in the shape in the vicinity of the moisture amount detection unit 30, and therefore such an extremely simple and compact shape can be employed. Needless to say, all or part of the swing member 20 may be configured to be detachable from the main body 10 together with the moisture amount detection unit 30 also in this case.

Figure 6:
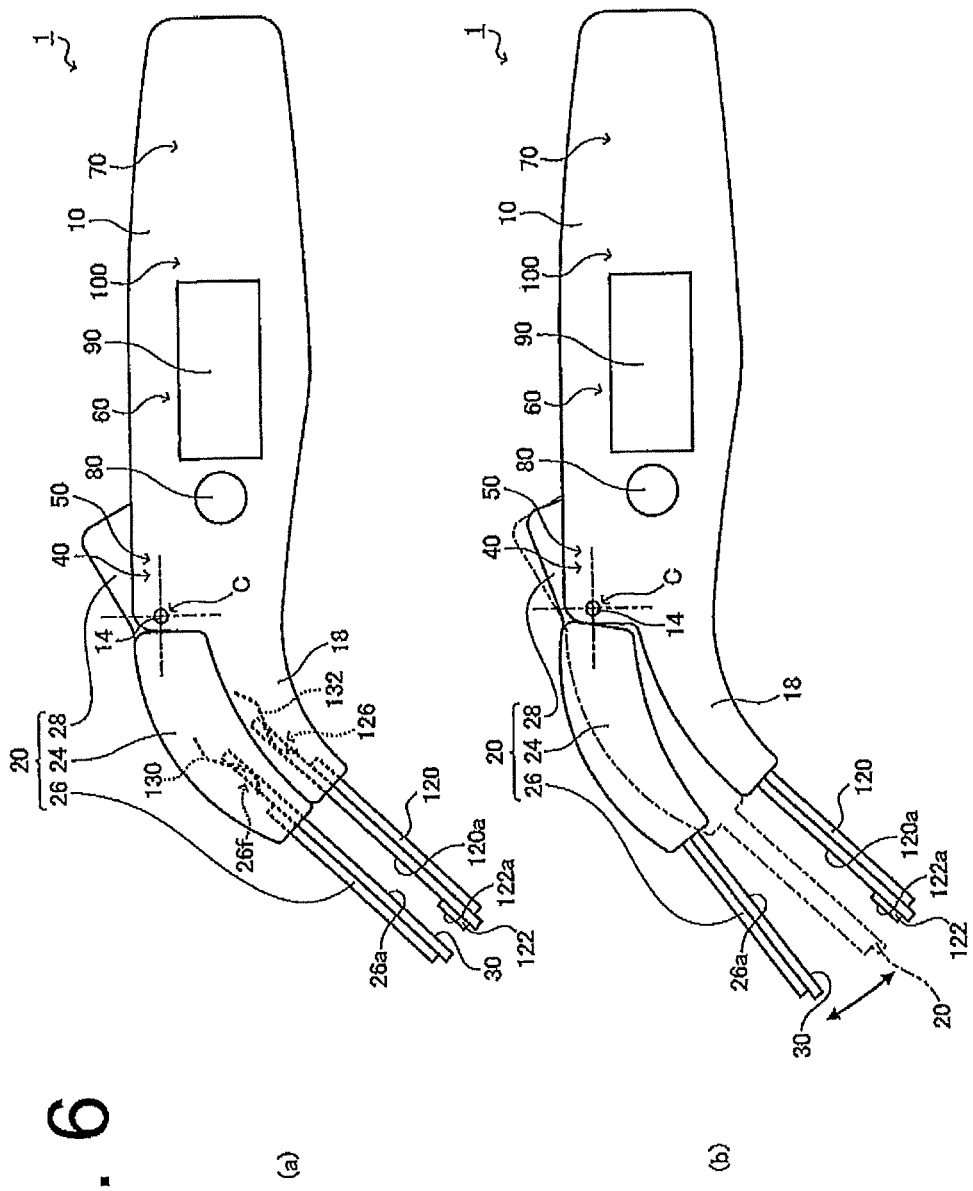
FIG. 6 and parts (a) and (b) thereof are schematic front views illustrating an intraoral moisture measuring device according to a second embodiment of the present invention.

An intraoral moisture measuring device 2 according to a second embodiment of the present invention will be described next. In the following description, elements same as those in the intraoral moisture measuring device 1 according to the first embodiment will be denoted by the same reference numerals throughout the drawings and the description thereof will be omitted. Only elements different from the first embodiment will be described. FIGS. 6(a) and 6(b) are schematic front views of the intraoral moisture measuring device 2 according to this embodiment.

As shown in these figures, the intraoral moisture measuring device 2 (hereinafter simply referred to as the measuring device 2) is obtained by adding a support member 120 for supporting a measurement site from its rear side, i.e., the side opposite to a moisture amount detection unit 30, to the configuration of the measuring device 1 of the first embodiment. In other words, in the measuring device 2 of this embodiment, a lip, a tongue, a cheek, or the like is interposed between the moisture amount detection unit 30 and the support member 120, and this allows the moisture amount detection unit 30 to be surely and stably abutted against the measurement site positioned therebetween.

A swing member 20 of this embodiment is constituted by: a slightly-curved fixed part 24 positioned closer to a main body 10; and a detachable part 26 detachably attached to the fixed part 24 and provided with the moisture amount detection unit 30 on the tip side thereof. The swing member 20 also includes an operation unit 28 extended on the side opposite to the moisture amount detection unit 30 with respect to a swing shaft 14. By operating the operation unit 28 with the index finger or thumb of a hand holding the main body 10, the swing member 20 can be easily swung. Moreover, an engagement member 130 for fixing the detachable part 26 is disposed inside the fixed part 24 of the swing member 20. The engagement member 130 is made of a suitable metal capable of elastic deformation, for example.

The support member 120 is detachably attached to an extended part 18 extended in a slightly curved manner from the main body 10 under the fixed part 24 of the swing member 20. The tip of the support member 120 is provided with a protrusion 122 at a position facing the moisture amount detection unit 30. Moreover, an engagement member 132 for fixing the support member 120 is disposed inside the extended part 18. The engagement member 132 is made of a suitable metal capable of elastic deformation, for example, as with the engagement member 130.

The detachable part 26 of the swing member 20 and the support member 120 project so as to be approximately parallel to each other in a direction oblique to the longitudinal direction of the main body 10. With this configuration, the moisture amount detection unit 30 and the tip of the support member 120 are disposed at positions easier to interpose a lip, a tongue, a cheek, or the like therebetween when the main body 10 is held by a user.

Figure 7:
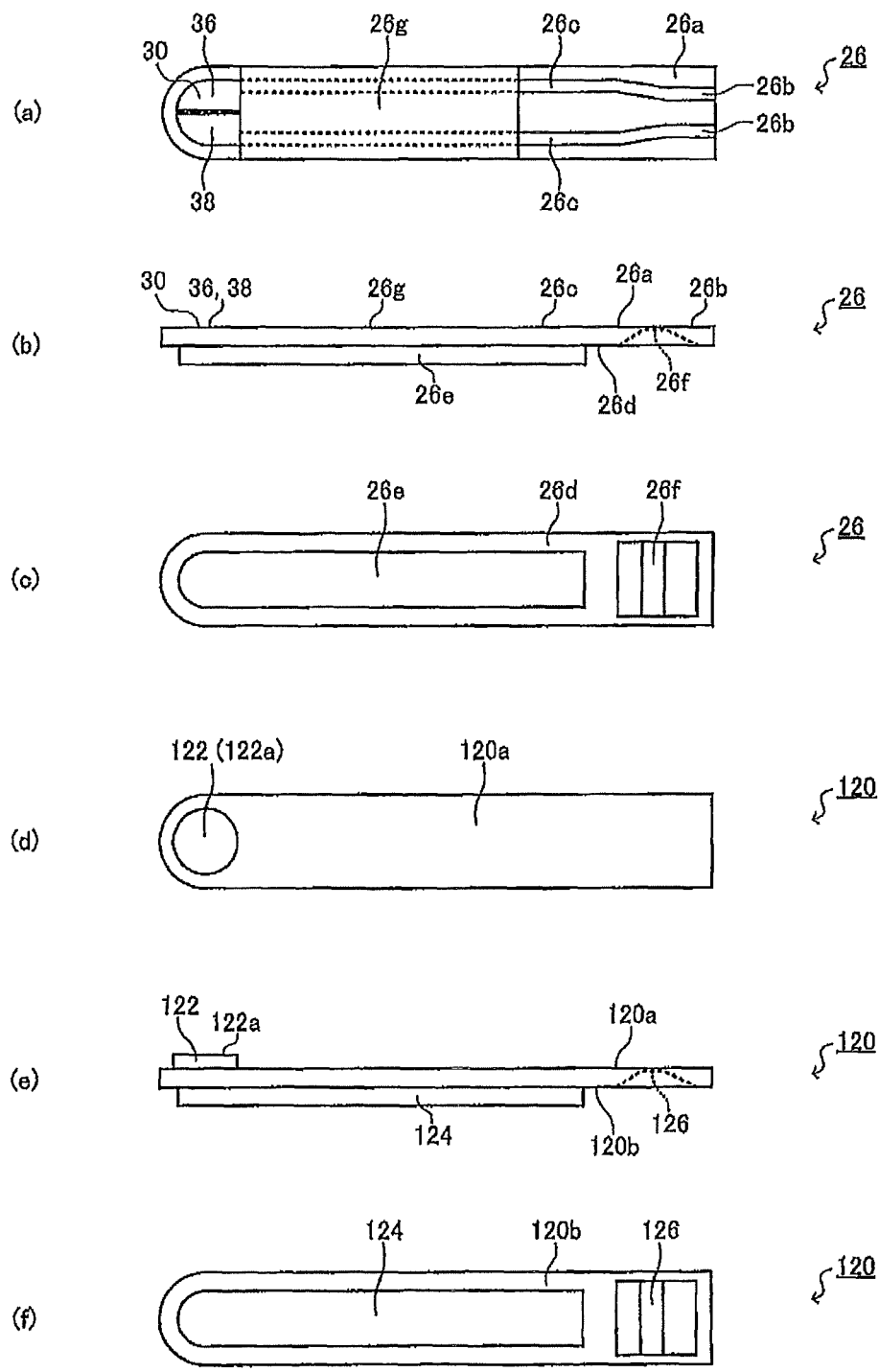
FIG. 7 illustrates a detachable part and a support member, with part (a) thereof being a schematic front view of a detachable part, part (b) thereof being a schematic bottom view of the detachable part, part (c) thereof being a schematic rear view of the detachable part, part (d) thereof being a schematic front view of a support member, part (e) thereof being a schematic bottom view of the support member, and part (f) thereof being a schematic rear view of the support member.

FIG. 7(a) is a schematic front view of the detachable part 26. FIG. 7(b) is a schematic bottom view of the detachable part 26. FIG. 7(c) is a schematic rear view of the detachable part 26. As shown in these figures, the detachable part 26 is formed in a generally rectangular plate shape with a rounded tip. A tip portion of a front surface 26a of the detachable part 26 is the moisture amount detection unit 30 and provided with a first electrode 36 and a second electrode 38. Moreover, two connection terminals 26b to be connected with terminals on the fixed part 24 side are provided on the base end side of the front surface 26a. Also, two wirings 26c connecting the first electrode 36 and the second electrode 38 with the two connection terminals 26b, respectively, are provided on the front surface 26a. A strengthening rib 26e for increasing bending rigidity and an engagement groove 26f for engaging with the engagement member 130 are provided on a rear surface 26d of the detachable part 26.

The first electrode 36, the second electrode 38, the connection terminals 26b, and the wirings 26c are formed by electrically-conductive thin films disposed on the front surface 26a. Moreover, the first electrode 36, the second electrode 38, and the wirings 26c are covered with an insulating layer, and thus the moisture amount detection unit 30 can be brought into direct contact with the measurement site. Furthermore, the wirings 26c are covered with a shield 26g made of an electrically-conductive thin film via the insulating layer therebetween. This prevents capacitance between the two wirings 26c from affecting the measurement of a moisture amount.

In other words, the detachable part 26 of this embodiment as is functions as part of the swing member 20 by extending the substrate 34 of the conventional sensor 32 in the first embodiment toward the main body 10. Furthermore, in this embodiment, providing the shield 26g makes it possible to maintain accuracy in the measurement of a moisture amount while the wirings 26c are formed by the electrically-conductive thin films. This allows the moisture amount detection unit 30 and the detachable part 26 to be configured extremely simply and inexpensively. Thus, the cost when the detachable part 26 is made disposable can be reduced.

As with the substrate 34, a suitable material such as a resin or ceramic, for example, can be employed as a material for the detachable part 26. A suitable material such as copper or aluminum, for example, may be employed as a material for the electrically-conductive thin films forming the first electrode 36, the second electrode 38, and the like. The insulating layer with which the first electrode 36, the second electrode 38, and the wirings 26c are covered may be formed by coating of an ultraviolet curable resin, for example. Alternatively, such an insulating layer may be formed by a resin film, for example, disposed on the first electrode 36, the second electrode 38, and the wirings 26c.

As with the first electrode 36, the second electrode 38, and the like, a suitable material such as copper or aluminum, for example, can be employed as a material for the electrically-conductive thin film forming the shield 26g. Moreover, an additional insulating resin film, for example, may be disposed between the insulating layer and the shield 26g so as to adjust the distance between the wirings 26c and the shield 26g and thereby optimize the shielding effect of the shield 26g.

FIG. 7(d) is a schematic front view of the support member 120. FIG. 7(e) is a schematic bottom view of the support member 120. FIG. 7(f) is a schematic rear view of the support member 120. As shown in these figures, the support member 120 is formed in a generally rectangular plate shape with a rounded tip as with the detachable part 26. The protrusion 122 having a generally cylindrical shape is provided at the tip of a front surface 120a of the support member 120. As with the detachable part 26, a strengthening rib 124 for increasing bending rigidity and an engagement groove 126 for engaging with the engagement member 132 are provided on a rear surface 120b of the support member 120.

In this embodiment, the support member 120 is provided with the protrusion 122 having a generally cylindrical shape. The measurement site is supported from its rear side by an upper surface 122a, having a generally flat shape, of the protrusion 122. This allows the moisture amount detection unit 30 to be abutted against the measurement site in a generally uniform and stable manner. Moreover, the support member 120 and the detachable part 26 are formed in approximately the same shape in this embodiment. This achieves the commonality of the parts, thereby further reducing the cost of the detachable part 26 and the support member 120.

Figure 8:
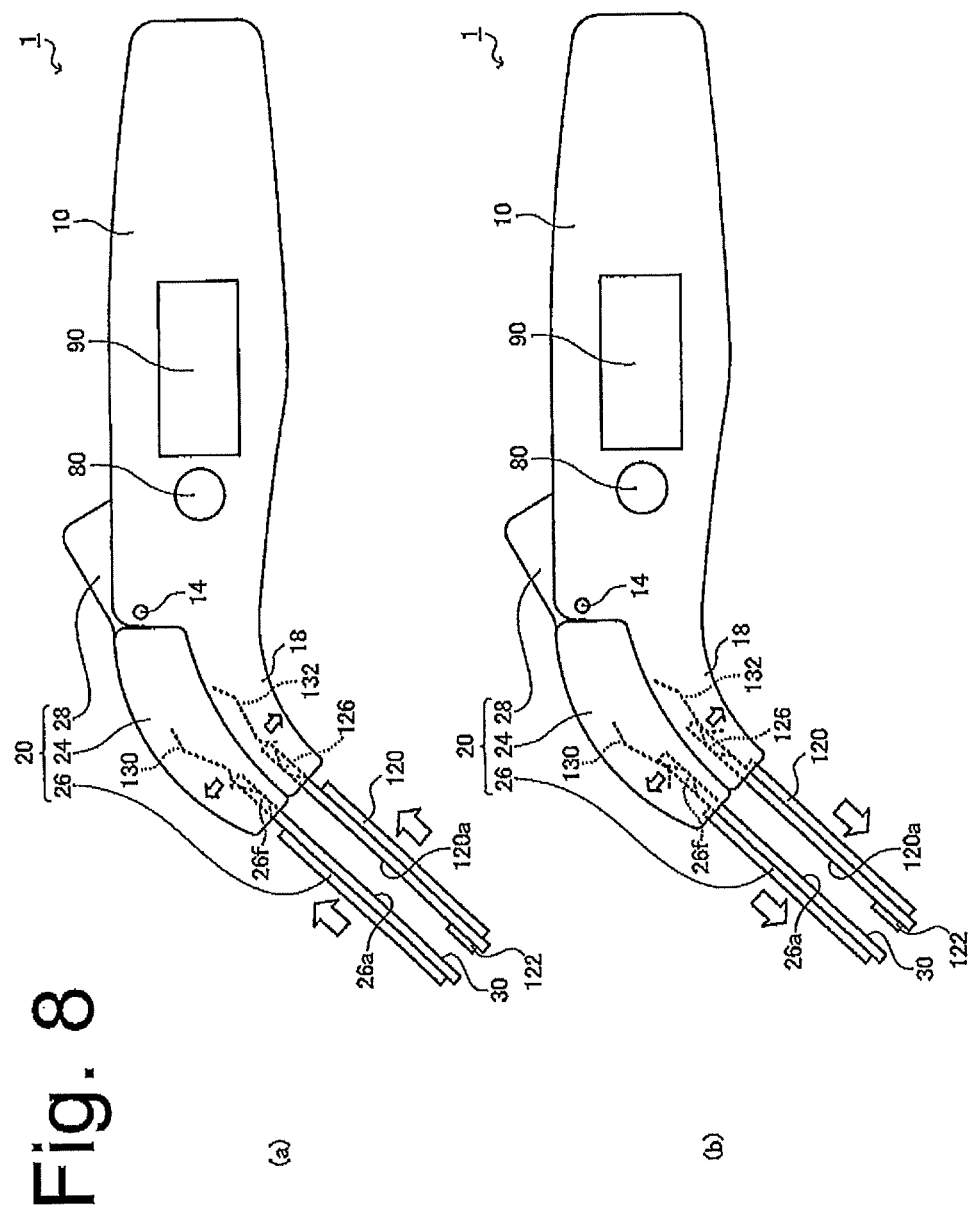
FIG. 8 illustrates the detachable part and the support member, with part (a) thereof being a schematic front view illustrating a state when the detachable part and the support member are being attached and part (b) thereof being a schematic front view illustrating a state when the detachable part and the support member are being removed.

FIG. 8(a) is a schematic front view illustrating a state when the detachable part 26 and the support member 120 are being attached. FIG. 8(b) is a schematic front view illustrating a state when the detachable part 26 and the support member 120 are being removed. In order to attach the detachable part 26 to the fixed part 24, the detachable part 26 is inserted, from the base end side thereof, into the fixed part 24 along a guiding member (not shown) with the front surface 26a facing the support member 120 as shown in FIG. 8(a). The engagement member 130 elastically deformed by the insertion of the detachable part 26 is fitted into and engaged with the engagement groove 26f. The detachable part 26 is thereby fixed to the fixed part 24.

When the detachable part 26 is fixed to the fixed part 24, the connection terminals 26b are connected to the terminals (not shown) in the fixed part 24. This achieves electrical connection between the moisture amount detection unit 30 and the control unit 60. In other words, simply by inserting the detachable part 26 into the fixed part 24 in the longitudinal direction thereof, the detachable part 26 can be attached to the fixed part 24 in an extremely easy manner.

In order to remove the detachable part 26 from the fixed part 24, all it takes is to pull the detachable part 26 toward the tip side thereof as shown in FIG. 8(b). Pulling the detachable part 26 toward the tip side causes the engagement member 130 to be guided by a slope provided in the engagement groove 26f and thereby disengaged from the engagement groove 26f. Thus, the detachable part 26 can be directly removed from the fixed part 24.

Similarly, in order to attach the support member 120 to the main body 10, the support member 120 is inserted, from the base end side thereof, into the extended part 18 along a guiding member (not shown) with the front surface 120a facing the detachable part 26 and the engagement member 132 is then engaged with the engagement groove 126. The support member 120 can be removed from the main body 10 simply by pulling the support member 120 toward the tip side thereof.

As described above, the detachable part 26 and the support member 120, which are the parts to be in contact with a subject to be measured, can be replaced in an extremely easy manner in this embodiment. In other words, without being bothered by, for example, the replacement of the cover 110 or the like, or the washing and sterilization of the components in the device, an appropriate hygienic condition can be surely maintained while measuring intraoral moisture in a simple and prompt manner.

Figure 9:
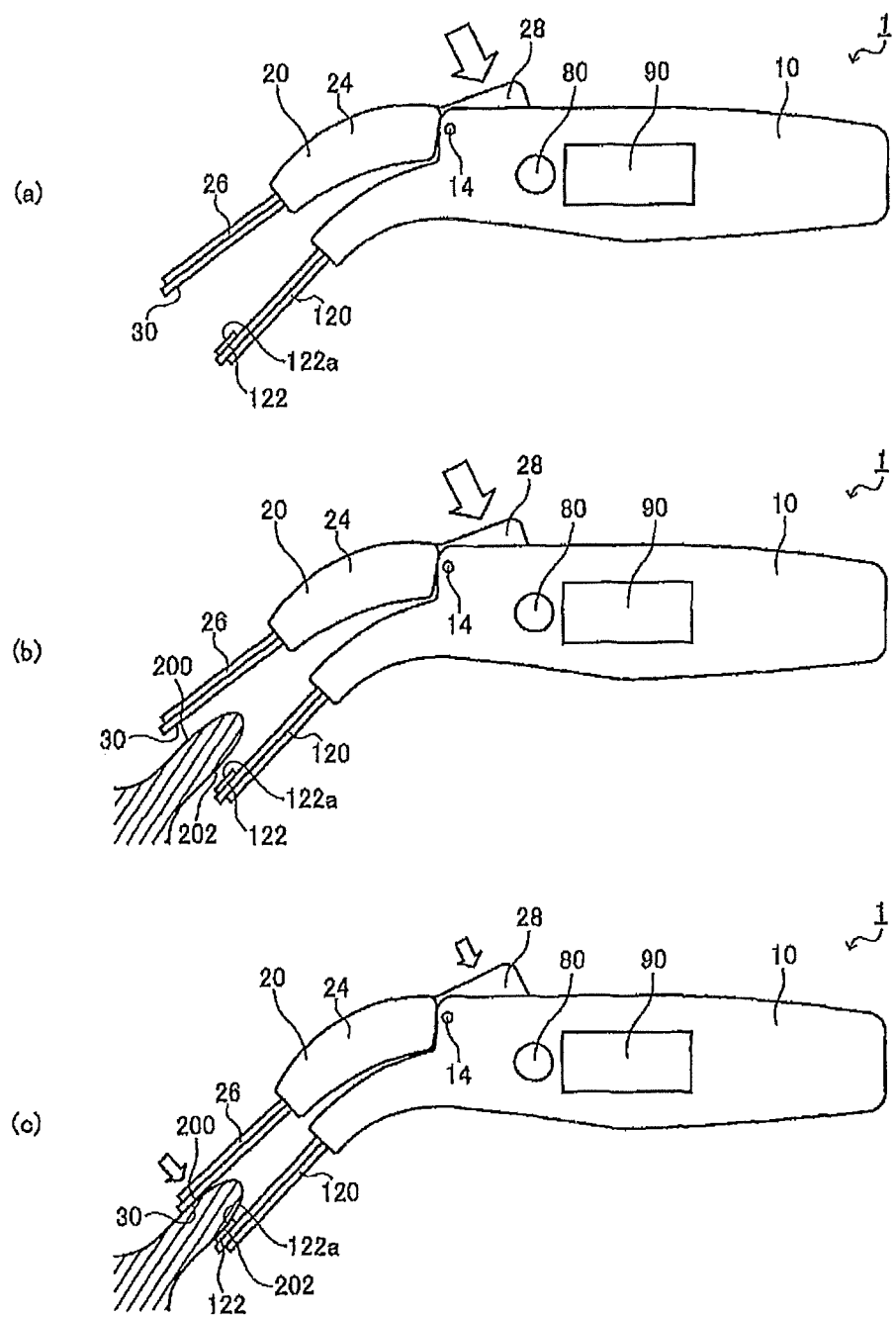
FIG. 9 is a schematic view of a method, with parts (a) to (c) thereof being schematic views illustrating a method of using the intraoral moisture measuring device.

A method of using the measuring device 2 will next be described. FIGS. 9(a) to 9(c) are schematic views illustrating the method of using the measuring device 2. In order to measure intraoral moisture by the measuring device 2, the detachable part 26 and the support member 120 newly prepared or the detachable part 26 and the support member 120 washed and sterilized are first attached to the fixed part 24 and the main body 10. Next, an operation button 80 is operated to turn on the power supply of the measuring device 2. This starts the measurement of pressing force by pressing force measuring means 64.

Next, the operation unit 28 is pressed to swing the swing member 20 and thereby set the moisture amount detection unit 30 apart from the support member 120 as shown in FIG. 9(a). At this time, the measurement of a moisture amount is prevented from starting by causing the pressing force by the biasing member 40 to exceed the upper limit of the appropriate range. Next, the measuring device 2 is disposed such that a lip, for example, of a subject to be measured is positioned between the moisture amount detection unit 30 and the support member 120 to cause the moisture amount detection unit 30 to face a measurement site 200 as shown in FIG. 9(b). Thereafter, while gradually reducing the pressing force to the operation unit 28, the moisture amount detection unit 30 is abutted against the measurement site 200 and the protrusion 122 of the support member 120 is abutted against a rear side 202 of the measurement site 200. The pressing force to the measurement site 200 by the moisture amount detection unit 30 thereby falls within the appropriate range, and the measurement of a moisture amount is thus started.

Although its diagrammatic representation is omitted, an adjustment mechanism for adjusting the biasing force of the biasing member 40 may be provided and the pressing force may be adjusted by this adjustment mechanism. Alternatively, the pressing force may be adjusted by replacing the detachable part 26 and the support member 120 with those having different shapes depending on a thickness around the measurement site 200, for example.

As just described, with the measuring device 2 of this embodiment, the moisture amount detection unit 30 can be stably abutted against the measurement site 200 with an appropriate pressing force even in an unstable portion such as a lip or a tongue. Thus, the measurement of a moisture amount in such a measurement site 200 can be performed with high accuracy. Moreover, the pressing force can be stably enhanced by the support member 120. This allows for the measurement of a moisture amount at a position deeper than that in the conventional techniques. In other words, the measuring device 2 of this embodiment allows for the measurement of a moisture amount in a labial minor salivary gland, which is difficult to achieve with the conventional techniques. Thus, the diagnosis of the Sjogren syndrome can be simplified.

As described above, the measuring devices 1 and 2 of the aforementioned embodiments each include: the swing member 20 that swings with respect to the main body 10 about the predetermined swing center C; the moisture amount detection unit 30 provided at the tip of the swing member 20 for detecting a moisture amount by being directly or indirectly abutted against the measurement site 200 in a mouth; and the biasing member 40 for biasing the swing member 20 in one of the swing directions.

With such a configuration, intraoral moisture can be measured in a simple and highly-accurate manner. Specifically, the combination of the swing member 20 and the biasing member 40 allows the moisture amount detection unit 30 to be abutted against the measurement site 200 with an appropriate pressing force. Thus, a moisture amount can be measured with high accuracy. Moreover, the combination of the swing member 20 and the biasing member 40 allows for the optimization of the pressing force without complicating the structure in the vicinity of the moisture amount detection unit 30. This facilitates, for example, the washing and sterilization of the moisture amount detection unit 30 and its adjacent part. In addition, the moisture amount detection unit 30 and its adjacent part can achieve a reduced cost and can therefore be easily made disposable.

Moreover, the swing center C is disposed in the main body 10. With such a configuration, the biasing member 40 can be disposed away from the moisture amount detection unit 30. Consequently, the structure around the moisture amount detection unit 30 can be simplified, and thus easily washed, sterilized, or made disposable.

Moreover, the measuring devices 1 and 2 each include the pressing force detection unit 50 for detecting a pressing force to the measurement site 200 by the moisture amount detection unit 30. With such a configuration, whether the pressing force is appropriate can be determined accurately, and a moisture amount can therefore be measured with high accuracy.

Moreover, the pressing force detection unit 50 is disposed inside the main body 10. With such a configuration, the structure around the moisture amount detection unit 30 can be simplified, and thus easily washed, sterilized, or made disposable.

Moreover, the measuring devices 1 and 2 each include the control unit 60 that controls the moisture amount detection unit 30 and the pressing force detection unit 50. The control unit 60 includes the pressing force determination means 66 for determining if the pressing force detected by the pressing force detection unit 50 falls within the appropriate range. With such a configuration, the measurement of a moisture amount can be performed after whether the pressing force falls within the appropriate range is determined. The moisture amount can therefore be measured with high accuracy.

Moreover, the control unit 60 includes the measurement starting means 68 that starts moisture amount measurement when the pressing force detected by the pressing force detection unit 50 falls within the appropriate range. With such a configuration, a moisture amount can be measured only when the pressing force falls within the appropriate range, and the moisture amount can therefore be measured with high accuracy.

Moreover, the control unit 60 may include the measurement stopping means for stopping the moisture amount measurement when the pressing force detected by the pressing force detection unit 50 falls outside the appropriate range. With such a configuration, a measurement result obtained when a pressing force falls outside the appropriate range during the measurement of a moisture amount can be eliminated, and therefore moisture amount measurement can be performed with high accuracy.

Moreover, at least part of the swing member 20 may be configured to be detachable from the main body 10 together with the moisture amount detection unit 30. With such a configuration, the moisture amount detection unit 30 and its adjacent part can be easily washed, sterilized, or made disposable. Thus, an appropriate hygienic condition can be maintained.

Moreover, the swing member 20 in the measuring device 2 includes the detachable part 26 which is detachable from the main body 10 together with the moisture amount detection unit 30. The detachable part 26 is provided with the first electrode 36 and the second electrode 38 included in the moisture amount detection unit 30 and the wirings 26*c* connected to the first electrode 36 and the second electrode 38. The first electrode 36, the second electrode 38, and the wirings 26*c* are formed by the electrically-conductive thin films disposed in the detachable part 26. With such a configuration, the detachable part 26 can be configured extremely simply and inexpensively. Thus, the detachable part 26 can be easily washed, sterilized, or made disposable.

Moreover, the wirings 26*c* in the measuring device 2 are covered with the shield 26*g* formed by the electrically-conductive thin film. With such a configuration, the wirings 26*c* can be prevented from affecting the measurement of a moisture amount even when the wirings 26*c* are formed simply and inexpensively by the electrically-conductive thin films. Thus, measurement accuracy can be maintained.

Moreover, the measuring device 2 includes the support member 120 for supporting the rear side 202 of the measurement site 200. This allows the moisture amount detection unit 30 to be stably abutted against the measurement site 200 with an appropriate pressing force even in an unstable portion. Moreover, since a pressing force can be stably enhanced, moisture amount measurement at such a position that the measurement has been difficult to achieve with the conventional techniques can be carried out.

Moreover, the support member 120 includes the protrusion 122 protruded toward the rear side 202 of the measurement site 200. The protrusion 122 includes the generally flat-shaped surface (the upper surface 122a) to be abutted against the rear side 202 of the measurement site 200. This allows the moisture amount detection unit 30 to be abutted against the measurement site 200 in a generally uniform and stable manner. Thus, a moisture amount can be measured with high accuracy.

While the embodiments of the present invention have been described above, the intraoral moisture measuring device of the present invention is not limited to the aforementioned embodiments. It is to be understood that various modifications are possible without departing from the scope of the present invention. For example, the shapes of the components in the measuring devices 1 and 2, such as the main body 10 and the swing member 20, are not limited to the shapes described in the aforementioned embodiments, and other shapes can be employed as desired. Moreover, the biasing member 40 may be a coiled spring or a torsion spring, for example, without being limited to the flat spring. Moreover, the pressing force detection unit 50 may be provided in a region other than the biasing member 40. Needless to say, the configuration of the second embodiment, e.g., the configuration of the detachable part 26, may be applied to the first embodiment.

When the appropriate range of the pressing force can be visually checked on the basis of the swing angle of the swing member 20, the pressing force detection unit 50, the pressing force measuring means 64, and the pressing force determination means 66 may be omitted. In this case, a measurement starting button may be further provided in the main body 10 so that moisture amount measurement is started by the operation of the measurement starting button by a user.

The measuring devices 1 and 2 each may be configured to include a communication unit for communicating with an external computer or the like and to be capable of transmitting stored measurement results, for example, to the external computer or the like. The control unit 60, the power supply unit 70, the operation button 80, the display unit 90, and the sound output unit 100, for example, may be provided outside the main body 10, and these may be configured by an existing computer.

The functions and effects described in the aforementioned embodiments are merely the listing of the most preferred functions and effects obtained by the present invention. Functions and effects of the present invention are not limited thereto.

INDUSTRIAL APPLICABILITY

The intraoral moisture measuring device according to the present invention can be used in the fields such as various types of oral care and various diagnoses relating to xerostomia in medical institutions or the like.

The invention claimed is:

1. An intraoral moisture measuring device comprising:
a swing member that swings with respect to a main body about a predetermined swing center;
a capacitance sensor provided at a tip of the swing member, the capacitance sensor being configured to detect a moisture amount by being directly or indirectly abutted against a tongue in a mouth;
an elastic member being elastically deformed when the swing member swings in one of a plurality of swing directions; and
a controller configured to control the capacitance sensor to start automatically measuring the moisture amount of the tongue when a pressing pressure of the capacitance sensor caused by a restoring force of the elastic member becomes within an appropriate range due to a swinging motion of the swing member, and to stop automatically measuring the moisture amount of the tongue when the pressing pressure of the capacitance sensor caused by the restoring force of the elastic member falls outside an appropriate range due to loosening of the swinging motion of the swing member;
wherein the controller configured to control the capacitance sensor is configured to start automatically measuring the moisture amount of the tongue when a swing angle of the swing member falls in a range of 30% or more of a full swing range of the swing member.

2. The intraoral moisture measuring device according to claim 1, wherein the full swing range of the swing member is 20 degrees or less.

* * * * *